United States Patent [19]

Wilkins

[11] Patent Number: 5,290,701
[45] Date of Patent: Mar. 1, 1994

[54] MICROBIAL DETECTION SYSTEM AND PROCESS

[76] Inventor: Judd R. Wilkins, 281 Littletown Quarter, Williamsburg, Va. 23185

[21] Appl. No.: 751,182

[22] Filed: Aug. 28, 1991

[51] Int. Cl.[5] .................. C12M 1/10; C12Q 1/02; G06F 15/00; G06K 7/00
[52] U.S. Cl. .................................. 435/312; 435/29; 435/39; 435/40; 435/287; 435/289; 435/291; 435/293; 435/300; 435/301; 422/64; 436/43; 364/413.01; 364/555; 364/924.2; 382/58; 382/6
[58] Field of Search .............. 435/29, 287, 289, 300, 435/301, 312, 34, 39, 40, 291, 293, 808, 809; 436/43; 364/413.01, 555, 924.2; 382/6, 58; 422/64

[56] References Cited

U.S. PATENT DOCUMENTS

| | | |
|---|---|---|
| 4,338,024 | 7/1982 | Bolz . |
| 4,451,433 | 5/1984 | Yamashita et al. ............... 422/64 |
| 4,521,512 | 6/1985 | Silman ........................... 435/35 |
| 4,526,865 | 7/1985 | Silman ........................... 435/35 |
| 4,665,553 | 5/1987 | Gershman . |
| 4,724,543 | 2/1988 | Klevecz . |
| 4,772,558 | 9/1988 | Hammann ....................... 435/300 |
| 4,794,450 | 12/1988 | Saite . |
| 4,845,552 | 7/1989 | Jaggi . |
| 4,856,073 | 8/1989 | Farber . |
| 4,859,586 | 8/1989 | Eisenberg ....................... 435/34 |
| 4,896,966 | 1/1990 | Boisseau et al. ................. 435/291 |
| 4,932,044 | 6/1990 | Williams . |
| 5,003,611 | 3/1991 | Miyake . |
| 5,112,745 | 5/1992 | Lorr ............................... 435/38 |

Primary Examiner—Michael G. Wityshyn
Assistant Examiner—Jane A. Williams
Attorney, Agent, or Firm—Wallace J. Nelson

[57] ABSTRACT

The presence and a quantitative estimate of microorganisms in a sample is determined by monitoring the growth of vertical subsurface colonies in a soft agar medium. A culture cell containing the sample-agar mixture is positioned on a rotating circular index table and, at an inspection station, a video camera monitors colony growth with an image processor and computer processing the output of the video camera. Select output parameters include, but are not restricted to, colony counts and growth rates, morphological variations and identification criteria.

10 Claims, 3 Drawing Sheets

MICROBIAL DETECTION SYSTEM AND PROCESS

FIELD OF THE INVENTION

This invention relates generally to microbial detection systems and relates specifically to apparatus and process for detecting and determining the rate of growth and quantitative concentrations of microbial organisms from a known or suspected contamination source.

BACKGROUND OF THE INVENTION

Historically, the accepted method for determining the presence of microorganisms in a sample has been to streak the surface of nutrient agar or inoculate tubes of nutrient broth. After incubation at suitable temperatures, discrete areas of growth known as colonies appear on the agar surface or the tubes of broth become cloudy from the microorganism growth.

Although numerous chemical and physical microbial detection methods have been introduced including, carbon labelled glucose, ATP reaction, impedance measurements, electrochemical techniques, and pressure measurements, the agar plate and tubes of broth are still de rigueur in many laboratories. This is particularly true of clinical laboratories where blood samples are routinely introduced into containers of nutrient broth and growth visually monitored by the technician. Resistance to new techniques results partially from the biological fact that the number of organisms required to evoke a chemical or physical response is also essentially the same number present when turbidity becomes visually apparent in the broth. Thus, a test sample containing 10 to 100 cells/ml requires eight to ten hours incubation, or longer to reach $10^5$ to $10^6$ cells per ml, the point when visual turbidity occurs or a physical or chemical measurement is productive.

Another historical method that impacts the present invention is the growth of colonies on the horizontal surface of agar in a Petri dish. The solidifying agent, agar is generally used in concentrations of 1-2% and is referred to as firm or hard agar. However, little attention has been paid to the vertical subsurface growth of microorganisms in an agar medium. In studies on the effect of gravity on subsurface growth, Wilkins, J. R. et al ("Effect of Gravity on the Colonial Morphology of Staphylococci in Soft Agar" *Applied Microbiology*, Vol 18, No. 4; pages 680–681, October 1969) described the effect of agar concentration on the subsurface colony morphology of *Staphylococcus aureus*. As discussed therein, at an agar concentration of 0.54% compact spherical colonies were produced, but as the agar concentration was reduced, the morphology varied from a tear drop shape to elongated, diffuse colonies in soft agar at a concentration of 0.18% agar. In addition, even though colony morphology was shown to be influenced by agar concentration, the subsurface growth can also be used to determine the number of organisms in the test sample. The same guidelines that govern the accuracy of surface counts where colonies are determined to arise from single cells or clumps would also be applicable to subsurface colonies. The morphology of developing subsurface colonies aids in identification of the test organism in the sample.

Another prior art method of determining microorganism growth rate is the pour plate procedure. In this technique the sample is added to 20–30 ml of molten agar at 45° C., mixed and at once poured into an empty Petri dish. After solidification at room temperature and incubation at 37° C., the colonies are examined and counted. As the growth medium employed in the pour plate method contains 1.5% agar, the majority of subsurface colonies are lenticular in shape with a few compact or disk-shaped colonies. In the present invention the microbial detection process differs markedly from this classical pour plate technique in two important aspects. First, the concentration of agar has been reduced from the usual 1.5% to a range of 0.16 to 0.40% which is generally referred to as soft agar. Next, the vertical depth of the agar medium has been increased by an order of magnitude from 10 mm in a Petri dish to 100 mm in a specially designed culture cell. Thus, the combination of soft agar and increased vertical depth of the agar medium permits the development of subsurface colonies as described by Wilkins, et al (*Applied Microbiology*; vol. 18, supra). In this report at an agar concentration of 0.54% compact spherical colonies were produced and, as the agar concentration was reduced, the morphology varied from tear shape to elongated, diffuse colonies in soft agar at a concentration of 0.18% agar.

Systems are still needed to study the morphology of developing colonies as an aid in identification of test organisms in a test sample. Also, a system for detecting both aerobic and anaerobic organisms, where special media conditions are required to exclude oxygen, is needed in the art. Further, a need still exists for a simple method of automatically determining the types and numbers of various microbes by conceptually blending electronic video and computer technology with microbiology into a workable system.

Accordingly, it is an object of the present invention to provide an automated system for detecting and enumerating the number and types of viable microorganisms present in fluid clinical samples of blood, urine, body and spinal fluids, samples from polluted water, food processing plants and fermentation liquids.

Another object of the present invention is to provide a culture cell that permits subsurface growth of organisms in a vertical plane.

A further object of the present invention is to provide a culture cell having two chambers for separately and simultaneously growing aerobic and anaerobic organisms.

Another object of the present invention is to provide a dual compartment culture cell having a hinged closure that permits ready access to either chamber for adding growth media and removing microbial growth for further laboratory testing.

A further object of the present invention is the provision of a video camera for recording the subsurface growth in a culture cell.

An additional object of the present invention is the provision of a computer and video camera system for capturing, digitizing, and computer processing microbial growth information to determine the presence and quantity of a suspect microorganism from a test sample.

SUMMARY OF THE INVENTION

According to the present invention the foregoing and additional objects are attained by providing an automatic system for determining the presence of, and recording the changes in microorganism growth over a period of time, in a variety of fluid clinical samples. The fluid samples capable of being studied by the present invention include, but are not limited to, blood, urine, body and spinal fluids, samples from polluted water, food processing plants and fermentation liquids.

One or more culture cells containing a specific growth media for the microorganism in question are inoculated with a sample from a suspect source, and placed in spaced relationship on an indexing table, contained within a suitable incubator set at the desired temperature for culture growth of the microorganism in question. A video camera is focused onto a specific area traversed by the indexing table and, as the indexing table rotates, or is indexed, each culture cell is stopped at the video camera location for a sufficient length of time to permit video recording of each culture cell and its contents at that location. This is continued for the desired period of time for incubation growth of the microorganism in question.

The video camera is connected to a compatible computer equipped with a flexible frame grabber board for capturing the video camera images where they are digitized and processed by the computer. The computer processing includes recording and supplying information of microorganism growth patterns during the incubation process with indication and analysis being made for the first growth, rate of growth, and final growth pattern and density. This information is compared with known microbial sample growth under the same conditions to thereby give indication of the microorganism presence and concentration in the test sample.

BRIEF DESCRIPTION OF THE DRAWINGS

A more complete appreciation of the invention and many of the attendant advantages thereof will be more readily apparent as the same becomes better understood by reference to the following detailed description when considered in connection with the accompanying drawings wherein.

DETAILED DESCRIPTION

Figure 1:
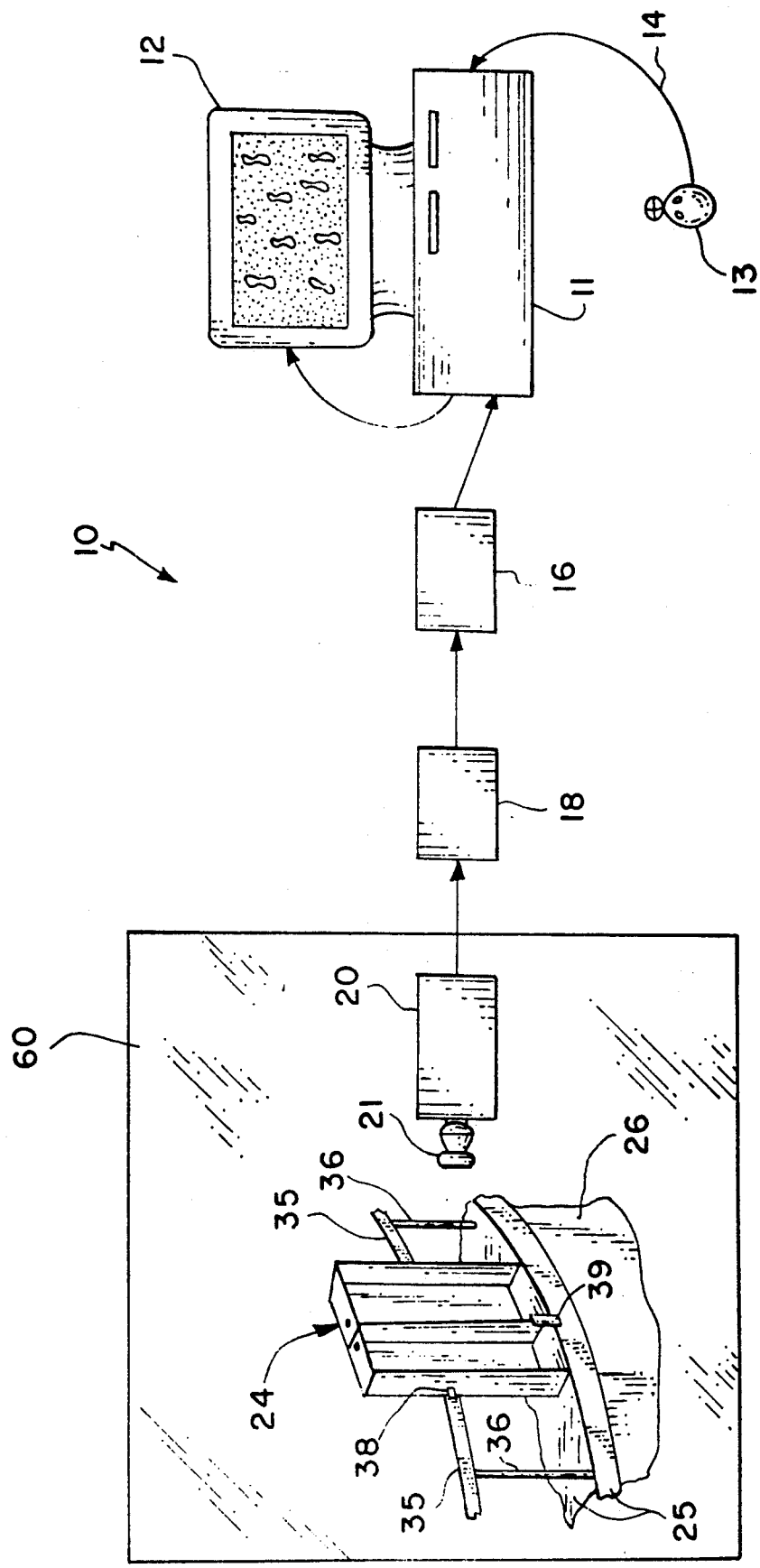
FIG. 1 is a part schematic representation of the apparatus component parts of the present invention.

Referring now to the drawings and more particularly to FIG. 1, the component parts of the microbial detection system of the present invention are schematically shown and designated generally by reference numeral 10. Detection system 10 includes a computer 11 and monitor 12, with a "mouse" control 13 attached thereto via cable 14. Computer 11 is provided with a frame grabber board 16 and a video processor 18. Video processor 18 is in operative connection with a video camera 20 provided with a close-up lens 21. Close-up lens 21 is disposed adjacent to and directed toward an individual culture cell 24. Culture cell 24 is one of many such cells releasably disposed about the circumference of a rotatable indexing table surface 25, as will be further explained hereinafter.

Indexing table surface 25 is rotatably disposed on an indexing table support housing 26. Video camera 20 and indexing table support housing 26 are contained within a walk-in incubator 60.

Figure 2:
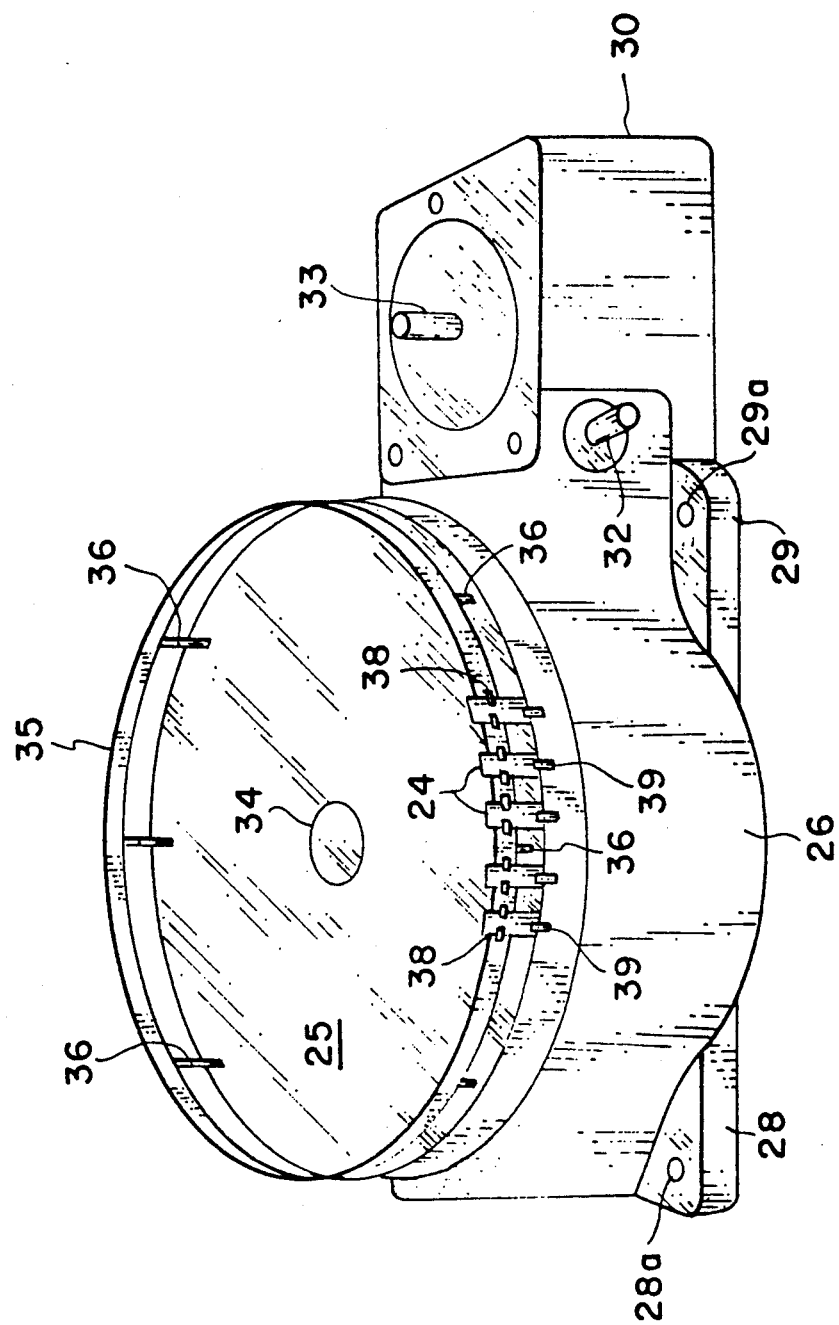
FIG. 2 is a part schematic representation of the index table transport system of the present invention and illustrating the support and retention mechanism for the culture cells thereon.

Referring now more particularly to FIG. 2, the details of indexing table surface 25 and indexing table support housing 26 will now be described. Index table support housing 26 is provided with a plurality of horizontally extending attachment ears, two of which are shown and designated by reference numerals 28,29 and two (not shown) on the opposite sides of housing 26. Each of attachment ears 28,29 (and the two not shown) are provided with a suitable bore therethrough to receive bolts for attachment of housing 26 to a suitable support surface within incubator 60. The bore for ears 28, 29 are designated, respectively, by reference numerals 28a and 29a.

Housing 26 is provided with a motor support extension 30. A horizontally disposed input shaft 32 and a vertical shaft 33 extend from motor support extension 30 and connect respectively with a drive motor and indexing control mechanism for driving, starting and stopping of rotating index table surface 25 about center post or axle 34. The drive motor and index control mechanism are conventional items and are omitted from the drawing in the interest of brevity.

A culture cell support rail 35 is supported in vertical spaced relationship to indexing table 25 via a plurality of vertical rail supports 36. Rail supports 36 are welded, bonded or otherwise conventionally secured in a circular pattern along, and spaced from the perimeter of indexing table surface 25. A plurality of culture cells 24 are disposed along the circumferential edge of indexing table surface 25 and are vertically supported thereon by support rail 35.

Suitable paired spring clips 38 are provided at spaced intervals along the exterior circumference of rail 35 and serve to releasably retain culture cells 24 attached thereto. Also, additional spring clips 39 are provided at spaced intervals along the exterior circumference of indexing table surface 25 to releasably engage culture cells 24, as a further retention aid therefor.

Figure 3:
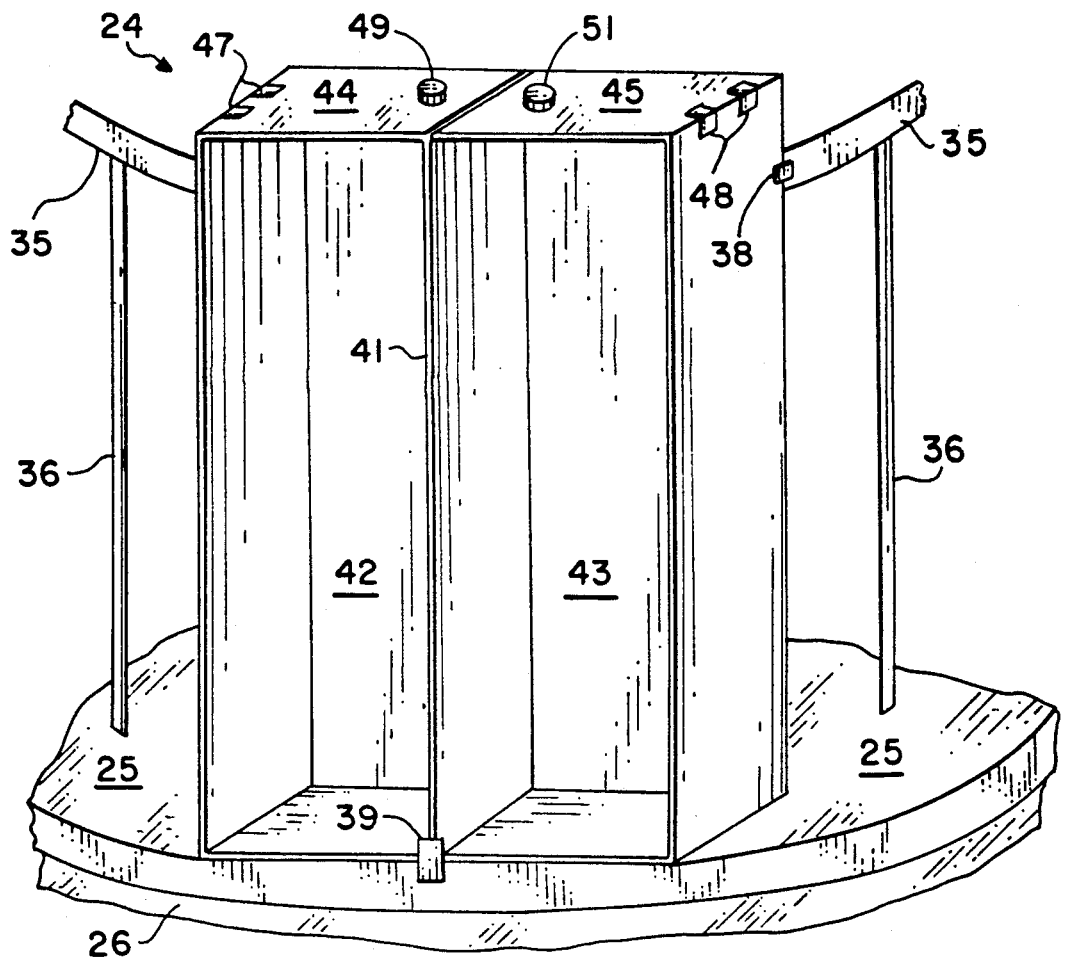
FIG. 3 is an enlarged view of one of the culture cells shown in FIGS. 1 and 2 and illustrating the dual chambers therein and further illustrating the support and retention mechanism for releasably securing the culture cell(s) on the index table shown in FIG. 2.

Referring now more particularly to FIG. 3, the details of an individual culture cell 24 will now be described. As described before, and as shown therein, culture cell 24 is of substantially rectangular configuration and is vertically disposed on the edge of the indexing table surface 25. Spring clip 39 serves to engage the bottom area of culture cell 24 and assists in releasably retaining each culture cell 24 in a vertical position against support rail 35. Paired spring clips 38 (one member of which is shown in this figure) engage the sides of each culture cell 24 to further secure the cell on indexing table surface 25.

Culture cells 24 are constructed of pyrex glass, or suitable hard clear plastic such as polyvinylchloride (PVC). In a specific embodiment, culture cell 24 is formed of bonded strips of polyvinylchloride bonded together to provide a cell having the dimensions of: width 70 mm (2¾ inches), length or height 110 mm (4¼ inches), depth 16 mm (⅝ inch), and a wall thickness of 1.0 mm (1/25 inch). A partition 41 having a length and side equal to the sides of cell 24, vertically divides cell 24 into two equal size chambers 42,43. For consistency, the left chamber 42 is denoted the aerobic chamber while chamber 43 is denoted the anaerobic chamber.

Obviously, either or both chambers may be employed for aerobic or anaerobic growth, as so desired.

Doors 44,45 are provided at the open end of respective chambers 42,43 and are connected to culture cell 24 via hinges 47,48. Knobs 49,51 are disposed on respective doors 44,45 to permit the introduction of media and inoculant, or sample, as well as the retrieval of growth after incubation is completed. Cells 24 are conventionally sterilized with ethylene oxide or similar cold sterilizing agents.

Figure 4:
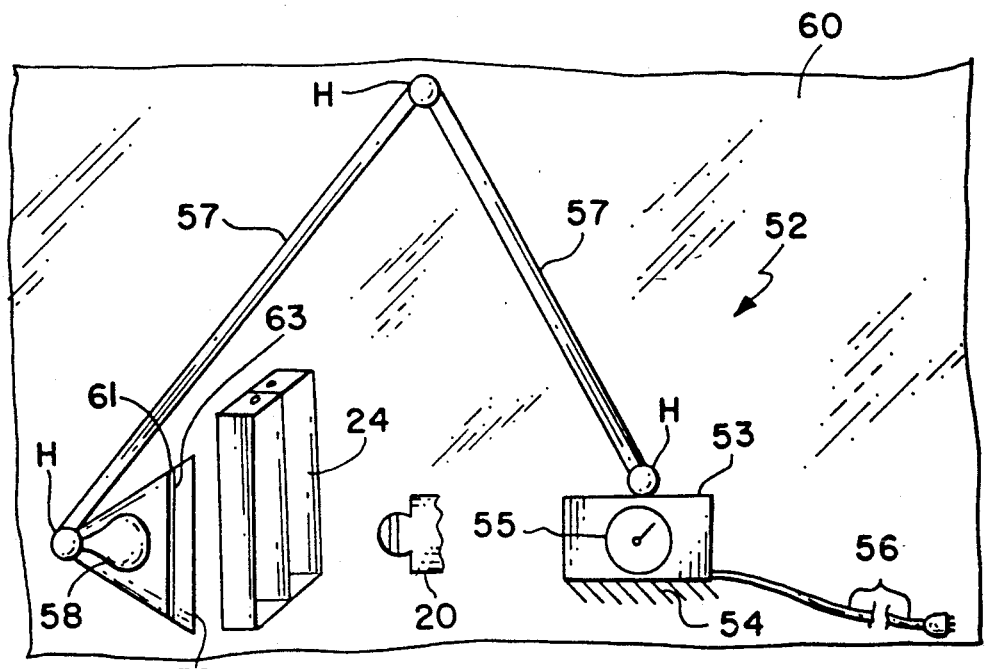
FIG. 4 is a part schematic representation of the light source structure employed to facilitate camera capture of the microorganism growth in the culture cells, according to the present invention.

Referring now more particularly to FIG. 4, a lighting system, designated generally by reference numeral 52, is shown. Lighting system 52 is employed to facilitate camera capture of the microorganism growth in each culture cell 24 and positioned so as not to interfere with the operation of camera 20 or the rotation of indexing table 25. As shown, lighting system 52 includes a light control housing 53 mounted in a conventional manner to a support surface 54 within incubator 60. A light control indicator dial 55 is provided on housing 52 and is designed to permit selection of the amount of light to be focused on culture cell in a conventional manner. An electric lead line 56 extends from light control housing 53 and is adapted to connect with a conventional 110 volt current source. A flexible arm 57, having a plurality of hinge connections H therein, extends from housing 52 and supports a light fixture containing a bulb 58 and shade 59. Shade 59 is provided with a slot 61 adapted to receive a suitable filter 63. Shade 59 is disposed behind and in position to direct light to shine on the rear of, or through, culture cell 24 to facilitate photographing thereof by camera 20.

In operation of one aspect of the present invention, 25 ml of nutrient broth containing 0.40% agar is melted and cooled to 45° C., the test sample added, mixed and poured into the left side, or aerobic chamber 42 of cell 24. For anaerobic growth, the agar concentration is reduced to 0.10% in a nutrient medium and poured in the anaerobic chamber 43 of cell 24. Alternatively, the agar may be omitted and a quantity of thioglycollate or other suitable reducing agent may be added to the nutrient medium for anaerobic growth. During solidification of the agar and incubation, the culture cell 24 remains in the upright or vertical position. The 25 ml of broth produces a column of 100 mm in the indicated chamber of culture cell 24. After the appearance of growth, the hinged doors 44,45 are opened to permit removal of the samples for identification using conventional microscopic, biochemical, serological and nucleic acid probe tests.

Referring again to FIG. 1, further details of the other component parts of the apparatus of the present invention will now be described. Computer 11 may be a conventional IBM computer or any one of its many clones. The Packard Bell 286 Personal Computer fulfills the requirements for computer 11 in the present invention. This computer has the necessary support features such as a one megabyte RAM on a mother board, 40 megabyte hard drive, 5¼ and 3½ floppy disk drives, mouse and a built in modem, VGA high resolution color monitor, fully MS-DOS software-compatible, and expansion ports. In addition, a 80286 microprocessor running at 12 MHZ is provided to make available the sophisticated software programs developed for the IBM-PC AT and compatibles.

Flexible frame grabber board 16 is a commercially available image capture device on a single computer board that provides an interface to high bandwidth, high resolution video sources. A number of vendors offer video frame capture devices that are compatible with the present invention including the SILICON VIDEO MUX, a flexible frame grabber available from EPIX, 310 Anthony Trail, Northbrook, Ill. 60062. Frame grabbers, in general, have the following characteristics; (1) digitize one or several frames from a video camera, or other video source, (2) allow the PC (personal computer) to process, analyze, and activate data, (3) transmit the image data, and (4) display the image data on black and white or color monitors. Specific characteristics of frame grabbers employed in the present invention include a menu driven program with mouse support that allows the user to: (1) select video input from the multiplexer, (2) select the sync source and video timing sequence, (3) display one image or a sequence of images at software selectable timed sequences, (4) same and load images to and from disk files with or with compression, (5) image addition, subtraction, differencing, averaging, and contrast matching on a pair of images, (6) edge detectors providing magnitude and gradient results, and (7) printing of images. The frame grabber SILICON VIDEO MUX, from EPIX fulfills these requirements and is compatible with the computer employed.

The capabilities of the frame grabber 16 and computer 11 combination are used to track the subsurface colony development following introduction of inoculum into the culture cell 24. Using the indexing table surface 25 described hereinbefore, individual culture cells 24 are captured, digitized and archived on an hourly (or less) basis. The first appearance of growth provides information on growth rate or generation time. For example, coliforms, with a generation time of less than twenty minutes, appear before slower growing organisms such as Pseudomonas or Corynebacterium, with doubling times of forty-fifty minutes. In addition, an alarm system at the first appearance of growth alerts the technician to permit further separate identification tests to be initiated.

For clinical samples the number of colonies appearing provides information on the severity of the infection. From a stored computer library of developing colony morphology for a variety of known organisms, individual frames or a sequence of frames are recalled from the stored data or files and compared with the unknown colony to aid in identification and enumeration thereof.

Since chamber 43 of culture cell 24 employed for growing anaerobes has 0.10% agar, compared with 0.16 to 0.40% agar for aerobic growth in chamber 42; subsurface colony morphology is not supported and detection is restricted to a cloudy appearance in the bottom portion of the chamber. Again, the rate of cloudy growth, its density and form, are all digitized and archived for reference and identification.

A suitable video camera 20 is available from a number of vendors and the one employed in a specific application of the present invention is a Dage MTI, series 68, instrumentation camera. This Dage camera is a high performance visual acquisition camera, designed to couple with a computer equipped with a flexible frame grabber board. This camera is further, capable of maximum performance in resolution (up to 1200 TV lines), stability, shading and geometry, and can be operated fully automatic or programmed for custom operation. In addition, this camera is equipped with a close-up lens 21 for the early detection of subsurface colony growth in the minimum size range of one to three mm. Camera 20 is positioned in front of a specific culture cell 24, on command from the computer software, two to four frames are captured by the flexible frame grabber 16, digitized and archieved by video processor 18 for further reference. Light system 52 provides maximum contrast enhancement of the developing subsurface colony. Bulb 58 in light system 52 may burn continuously or the system may be programmed to be illuminated only during camera operation. After a time interval necessary for the camera to record the culture growth in a specific cell, the next culture cell 24 on indexing table surface 25 moves into position and the process is repeated. Identification labels may be supported by base spring clips 39 or positioned directly on culture cells 24 so the image thereof is captured by camera 20, with the time and date for each cell being automatically generated internal to the computer.

Indexing table surface 25 and indexing table support housing 26 are parts of a commercially available index table available from a number of vendors. Index tables employ circular metal plates that rotate in clock-wise fashion and are programmable to stop at a station for a set period of time and then move on to the next station. The index table employed in the present invention is available from Jackson Machine Products, 690 Ajax Drive, Madison Heights, MI 48971-2480 and is available with either an air or hydraulic motor drive for rotating indexing table surface 25 and with standard size table surface diameters of either 23 or 28 inches. Basically, index tables consist of a circular metal plate (indexing table surface 25) a crank drive with "V" notching to provide accurate and smooth starts and stops of the support surface, an adjustable cam, limit switch, clutch, and motor. The details of these components are not illustrated or further described herein in the interest of brevity. In the present invention table surface 25 is a metal plate 48 inches in diameter that accommodates forty individual dual-chambered culture cells 24 releasably attached to the perimeter of support surface 25 by spring clips 39 and to support rail 35 via spring clips 38, as described hereinbefore. Support rail 35 is disposed along, and spaced internally from, the perimeter of support surface 25 and is constructed of one-half inch metal. Support rail is maintained spaced four inches above support surface 25 by eight vertical supports 36 welded or otherwise conventionally attached to the support surface 25 and to rail 35.

Indexing table surface 25 is programmed to position each culture cell 24 in front of video camera 20 on a one minute basis to allow frame capture by the computer 11 through frame grabber 16. Reflected back lighting enhances contrast of the developing colonies. The index table system (25, 26 etc.) and video camera 20 are positioned inside walk-in incubator 60, maintained at 37° C., to permit organism growth. Conventional connections to the computer are hardwired to the exterior of the incubator.

The output signal of video camera 20 is fed into video processor 18 that is provided with controls or 'Pots' that enable the operator to adjust and optimize brightness, contrast and resolution of the developing subsurface colonies. The output signal from video processor 18 is fed into the frame grabber board 16 which stores still frame images of the colonies for subsequent display on monitor 12, as controlled by the operator. A suitable control "mouse" 13 permits the operator to mark and count the developing colonies. Monitor 12 is of the RGB type which enables the color presentation to be controlled by signals from computer 11 with red, blue and green controls available for individual control.

It is thus seen that the present invention provides a novel automated system and process for improving the accuracy and reducing the man hours spent in detecting and enumerating the number and types of viable microorganisms present in fluid clinical samples of blood, urine, body and spinal fluids, samples from polluted waters, food processing plants and fermentation liquids.

Although the invention has been described relative to a specific embodiment thereof, it is not so limited and there numerous variations and modifications thereof that will be readily apparent to those skilled in the art in the light of the above description. It is therefore to be understood that, within the scope of the appended claims, the invention may be practiced other than as specifically described herein.

What is claimed as new and desired to be secured by Letters Patent of the United States is:

1. Apparatus for detecting the presence and an indication of the quantity of a specific microorganism in an agar culture, comprising:
    a plurality of culture cells each containing a quantity of nutrient broth containing an agar concentration in the range of 0.10% to 0.40% agar and inoculated with, a culture from a known or suspected microorganism source;
    retention means for retaining said plurality of culture cells in a spaced vertical arrangement;
    an incubator for housing said retention means and said plurality of culture cells;
    camera means in optical alignment with said retention means for photographing the culture growth in each of said plurality of culture cells at selected time intervals,
    means for interpreting photos of the culture growth pattern taken by said camera means which relates culture growth patterns to organism types and quantifies cell numbers in the original inoculum;
    each of said plurality of culture cells being provided with a substantially rectangular configured housing;
    each said rectangular configured housing having a vertical partition disposed substantially intermediate the width thereof and serving to divide said housing into first and second vertically disposed chambers;
    a separate cover for each of said first and said second vertically disposed chambers to permit sealing of each chamber and to provide access to each chamber for supplying nutrient agar to, and for removing microbial growth from, each said chamber; and
    hinge means securing each of said separate covers to a side of a said rectangular configured housing.

2. The apparatus of claim 1 wherein each of said first and said second vertically disposed chambers is provided with different concentrations of agar with the concentration of agar in said first vertically disposed chambers being selected to support growth of aerobic microorganisms and the concentration of agar in said second vertically disposed chambers being a fraction of that of said first chambers and selected to support anaerobic microorganism growth.

3. The apparatus of claim 2 wherein the concentration of agar in said first chambers is in the range of 0.16% to 0.40% agar and the concentration of agar in said second chambers is 0.10%.

4. The apparatus of claim 1 wherein said retention means for retaining said plurality of culture cells in a spaced vertical arrangement includes:
   a circular indexing table surface;
   a circular culture cell support rail disposed in spaced adjacency to the perimeter of said circular indexing table surface;
   a plurality of vertical rail supports attached to said circular indexing table surface and to said culture cell support rail;
   said plurality of vertical rail supports serving to fixedly attach said culture cell support rail to said circular indexing table surface, said culture cell support rail being spaced from said circular indexing table a distance equal to the length of said plurality of vertical rail supports.

5. The apparatus of claim 4 wherein said retention means further includes:
   a plurality of spring clips arranged in spaced pairs and attached to the perimeter of said culture cell support rail;
   said plurality of spring clips being spaced on said culture cell support rail to receive one culture cell in spring clipped retention between each of said spaced pairs of spring clips.

6. The apparatus of claim 5 wherein said retention means further includes:
   an individual spring clip attached to the perimeter of said circular indexing table surface and spaced from and substantially intermediate the position of each spaced pair of said spring clips attached to the perimeter of said culture cell support rail;
   each said individual spring clip attached to the perimeter of said circular indexing table surface serving to releasably engage the bottom area of a culture cell positioned between and spring clipped between each of said spaced pairs of spring clips.

7. The apparatus of claim 1 wherein said camera means is a video camera provided with a close-up lens and disposed in a fixed position within said incubator; and wherein said retention means includes an indexing table surface supported by a rotation mechanism for rotating and stopping said indexing table surface at selected intervals to position each of said plurality of culture cells in position to be photographed by said video camera for a specific period of time.

8. The apparatus of claim 7 including light means disposed adjacent to and directed toward each said culture cell when said culture cell is in position to be photographed by said video camera.

9. The apparatus of claim 8 wherein said light means includes a light bulb; a slotted light shade surrounding said light bulb and directing light toward said culture cell; and a filter disposed in said slotted light shade to maximize the contrast of a microorganism culture growing in said culture cell.

10. The apparatus of claim 4 wherein said means for interpreting photos of the culture growth pattern taken by said camera means includes a computer; a flexible frame grabber in connection with said computer for capturing the video camera images; a computer processor for digitizing the camera images, recording and supplying information of microorganism growth patterns during the incubation process with indication and analysis being made for the first growth, rate of growth, and final growth pattern and density; and said computer processor further comparing this information with known microbial sample growth under the same conditions to thereby give an indication of the microorganism presence and concentration in the culture growth.

* * * * *